United States Patent [19]

Troxler et al.

[11] 4,073,909

[45] Feb. 14, 1978

[54] ISOQUINOLINE COMPOUNDS

[75] Inventors: Franz Troxler; Erik Wiskott, both of Bottmingen, Switzerland

[73] Assignee: Sandoz Ltd., Basel, Switzerland

[21] Appl. No.: 664,968

[22] Filed: Mar. 8, 1976

Related U.S. Application Data

[63] Continuation-in-part of Ser. No. 511,690, Oct. 3, 1974, abandoned.

[30] Foreign Application Priority Data

Mar. 26, 1975 Switzerland .......................... 3876/75
Oct. 8, 1973 Switzerland ........................ 14307/73

[51] Int. Cl.² .................... A61K 31/47; C07D 217/04;
C07D 215/14; C07D 217/12
[52] U.S. Cl. ................ 424/258; 260/287 D;
260/288 A; 260/288 D
[58] Field of Search ........... 424/258; 260/288, 288 A,
260/288 D, 287 D

[56] References Cited

U.S. PATENT DOCUMENTS 2,612,503  9/1952  Ullyot .............................. 260/288 D
3,172,809  3/1965  De Salvo et al. ............... 260/288 D
3,340,266  9/1967  Howe et al. ......................... 260/288

FOREIGN PATENT DOCUMENTS 46-11,339  3/1971  Japan .............................. 260/288 D

OTHER PUBLICATIONS

Troxler et al. — Chem. Abst., vol. 72, col 66805j, (1970).
Anderson et al., Org. Chem., vol. 47, pp. 11202–11206, (1953).

*Primary Examiner*—Frederick E. Waddell
*Attorney, Agent, or Firm*—Gerald D. Sharkin; Robert S. Honor

[57] ABSTRACT

This invention provides new compounds of formula I,

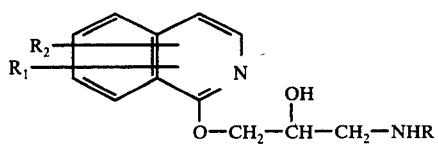

wherein
R is lower alkyl or cycloalkyl of 3 to 7 carbon atoms; cycloalkyl of 3 to 7 carbon atoms substituted by alkyl of 1 to 4 carbon atoms; α-dialkylpropinyl or α-dialkylallyl of 5 to 9 carbon atoms; hydroxyalkyl of 2 to 7 carbon atoms, the hydroxy group thereof being separated by at least two carbon atoms from the nitrogen atom to which R is bound; phenethyl; phenethyl substituted by halogen, alkyl or alkoxy of 1 to 4 carbon atoms; or adamantyl,
$R_1$ is hydrogen, halogen, alkyl or alkoxy of 1 to 4 carbon atoms, trifluoromethyl in the 5, 6 or 7 position, or a nitro or A—NH— group in the 4 or 5 position, wherein A is formyl or alkanoyl of 2 to 4 carbon atoms, and
$R_2$ is hydrogen, or, when $R_1$ is alkyl of 1 to 4 carbon atoms, also alkyl of 1 to 4 carbon atoms, or, when $R_1$ is alkoxy of 1 to 4 carbon atoms, also alkoxy of 1 to 4 carbon atoms,
with the general proviso that the 8 position of the isoquinoline ring is unsubstituted, and any halogen substituent which may present in the 3 or 4 position is other than fluorine, useful as β-blocking agents with metabolic effects.

52 Claims, No Drawings

ISOQUINOLINE COMPOUNDS

This is a continuation-in-part of our copending application Ser. No. 511,690 filed Oct. 3, 1974, now abandoned.

The present invention relates to new heterocyclic compounds.

In accordance with the invention there are provided new compounds of formula I,

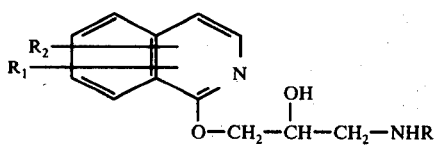

I wherein
- R is lower alkyl or cycloalkyl of 3 to 7 carbon atoms; cycloalkyl of 3 to 7 carbon atoms substituted by alkyl of 1 to 4 carbon atoms; α-dialkylpropinyl or α-dialkylallyl of 5 to 9 carbon atoms; hydroxyalkyl of 2 to 7 carbon atoms, the hydroxy group thereof being separated by at least two carbon atoms from the nitrogen atom to which R is bound; phenethyl; phenethyl substituted by halogen, alkyl or alkoxy of 1 to 4 carbon atoms; or adamantyl,
- $R_1$ is hydrogen, halogen, alkyl or alkoxy of 1 to 4 carbon atoms, trifluoromethyl in the 5, 6 or 7 position, or a nitro or A—NH— group in the 4 or 5 position, wherein A is formyl or alkanoyl of 2 to 4 carbon atoms, and
- $R_2$ is hydrogen, or, when $R_1$ is alkyl of 1 to 4 carbon atoms, also alkyl of 1 to 4 carbon atoms, or, when $R_1$ is alkoxy of 1 to 4 carbon atoms, also alkoxy of 1 to 4 carbon atoms,
  - with the general proviso that the 8 position of the isoquinoline ring is unsubstituted, and any halogen substituent which may present in the 3 or 4 position is other than fluorine.

When R is the alkyl or hydroxyalkyl radical defined above, the alkyl moiety is preferably branched, especially in an α position to the nitrogen atom to which it is bound. Specially preferred alkyl moieties are isopropyl, tert.butyl, 3-pentyl and tert. pentyl.

When R is cycloalkyl, this preferably is of 3 to 6 carbon atoms. Examples include cyclopropyl, cyclopentyl and cyclohexyl.

When R is cycloalkyl substituted by alkyl, the alkyl substituent thereof especially signifies methyl. Preferably there is one alkyl substituent. Preferably the substituent is in the 1 position. Examples of interesting alkylcycloalkyl groups are 1-methylcyclopropyl and 1-methylcyclohexyl.

When R is the α-dialkylpropinyl or α-dialkylallyl radical defined above, the alkyl groups thereof preferably are identical and especially signify methyl or ethyl.

When R is a phenethyl group substituted by the radicals defined above, this phenethyl radical especially is mono- or disubstituted. When it is substituted by halogen, halogen signifies fluorine, chlorine or bromine, preferably fluorine or chlorine. Any alkyl or alkoxy substituents of the phenethyl radical preferably contain 1 or 2, especially 1 carbon atom. At least one ring substituent is preferably in the para position.

When $R_1$ and/or $R_2$ are alkyl or alkoxy of 1 to 4 carbon atoms, these radicals especially contain 1 or 2, preferably 1 carbon atom.

When R, $R_1$ or $R_2$ contains halogen, this signifies fluorine, chlorine or bromine, preferably fluorine or chlorine.

Any carbon containing radical not particularly defined herein preferably has up to 5 carbon atoms.

Further, in accordance with the invention a compound of formula I may be obtained by a process comprising a. reacting a compound of formula II,

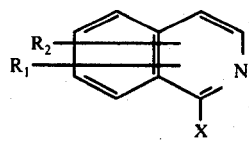

II wherein $R_1$ and $R_2$ are as defined above, and X is an anionic leaving group, with a compound of formula III,

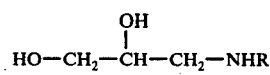

III wherein R is as defined above, or b. hydrolyzing a compound of formula IV,

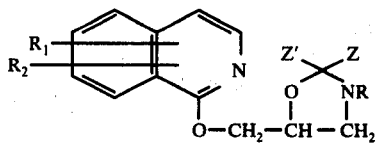

IV wherein R, $R_1$ and $R_2$ are as defined above, and

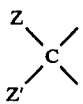

is a group capable of being split off during hydrolysis.

The process of the invention may be effected in a manner analogous to known methods.

The reaction in accordance with process variant (a) may, for example, be effected by allowing to stand a solution of a compound of formula II and a compound of formula III in an inert organic solvent, e.g. a lower alkanol such as ethanol. A basic condensation agent may be present, e.g. an alkali metal alcoholate such as potassium tert.butylate. The reaction temperature may vary between about 0° and about 80° C, but room temperature is conveniently used. The reaction may be accelerated by stirring. The reaction time depends, inter alia, on the reaction temperature.

X may be, for example, chlorine, bromine or lower alkylthio suchh as methylthio.

Process variant (b) may be effected under conventional conditions for the hydrolysis of oxazolidines. Z and Z' may be chosen such that the moiety Z.CO.Z' is an aliphatic or aromatic ketone or aldehyde. Examples are propionaldehyde, benzaldehyde and acetone. Such oxazolidines may be hydrolysed under acid conditions.

Suitable acids which may be used are especially dilute acids, e.g. between 0.5 and 3 N, e.g. 1N. Mineral acids, e.g. hydrochloric acid or sulphuric acid, may be used.

A convenient reaction temperature is between 0° and about 80° C.

The reaction time depends on the reaction conditions.

The resulting compounds of formula I may be isolated from the reaction mixture and purified in known manner.

Free base forms of compounds may be converted into acid addition salt forms in conventional manner and vice versa. Suitable acids for salt formation include organic acids such as maleic acid and fumaric acid and inorganic acids such as hydrochloric acid.

Compounds of formula II wherein X is chlorine or bromine are known or may be produced in a manner analogous to known methods.

Compounds of formula II wherein X is chlorine or bromine may be reacted with hydrogen sulphide to produce corresponding thiol compounds. The reaction may be carried out under conventional conditions, e.g. in methanol. Room temperature is a suitable reaction temperature.

The said thiol compounds may be converted into compounds of formula II, wherein X is alkylthio using conventional alkylation reactions.

A compound of formula III may for example be obtained by reacting 1,2-dihydroxy-3-chloropropane or glycidol with an amine of formula V,

   V wherein R is as defined above.

A compound of formula IV may be obtained by reacting a compound of formula II with a compound of formula VI,

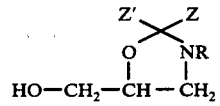   VI wherein R is as defined above.

The reaction may be effected in an inert organic solvent. The reaction is conveniently effected in the presence of a base, e.g. potassium tert.butylate. The reaction temperature may vary between room temperature and a slightly elevated temperature. The reaction may have duration of several hours.

A compound of formula VI may, for example, be obtained by reacting a compound of formula III with the appropriate aldehyde and ketone.

Insofar as the production of the starting materials is not described, these are known or may be produced in accordance with known processes, or in a manner analogous to the processes described herein or to known processes.

In the following non-limitative Examples all temperatures are indicated in degrees Centigrade and are uncorrected.

EXAMPLE 1

1-(2-hydroxy-3-isopropylaminopropoxy)-7-methoxy-isoquinoline [process variant b)]

1 g of 1-(3-isopropyl-2-phenyl-5-oxazolidinylmethoxy)-7-methoxy-isoquinoline is heated to 80° in 10 cc of 1 N hydrochloric acid for 10 minutes. The reaction mixture is extracted with ether. The ethereal phase is discarded, and the aqueous phase is made alkaline with potash, extracted with ether, the ether phase is dried over magnesium sulphate and concentrated, whereby a crystalline product is obtained which is treated in methanol with maleic acid. Ether is added, whereby 1-(2-hydroxy-3-isopropylaminopropoxy)-7-methoxyisoquinoline is obtained as hydrogen maleate. M.P. 144°-146°.

The 1-(3-isopropyl-2-phenyl-5-oxazolidinylmethoxy)-7-methoxy-isoquinoline, required as starting material, is obtained as follows:

0.3 g of potassium are dissolved in 15 cc of absolute tert.butanol, and 1.5 g of 1-chloro-7-methoxyisoquinoline and 1.7 g of 5-hydroxymethyl-3-isopropyl-2-phenyl-oxazolidine are added. The solution is heated to 50° for 1 hour, whereupon it is evaporated to dryness. The product is digested with water, extracted with ether, the ether phase is dried and the ether is distilled off. 1-(3-isopropyl-2-phenyl-5-oxazolidinylmethoxy)-7-methoxyisoquinoline is obtained as an oil.

The 5-hydroxymethyl-3-isopropyl-2-phenyloxazolidine, B.P. 133°-134° at 0.08 mm Hg, required for the reaction, is obtained by boiling 1,2-dihydroxy-3-isopropylaminopropane with an excess of benzaldehyde in benzene on a water separator.

1,2-dihydroxy-3-isopropylaminopropane, B.P. 96°-98° at 0.4 mm Hg, is obtained by heating 1,2-dihydroxy-3-chloropropane in a 15-fold excess of isopropylamine in a bomb tube to 100°.

EXAMPLE 2

1-(2-hydroxy-3-isopropylaminopropoxy)isoquinoline [process variant b)]

2.0 g of 1-(3-isopropyl-2-phenyl-5-oxazolidinylmethoxy)isoquinoline are heated to 50° for 1 hour with 20 cc of 1 N hydrochloric acid. The reaction mixture is extracted with methylene chloride. The methylene chloride phase is discarded and potash is added to the aqueous phase until an alkaline reaction is obtained, and then extraction is effected thrice with methylene chloride. These three extracts are dried over magnesiumm sulphate and concentrated. The residue is reacted in tetrahydrofuran with maleic acid to obtain 1-(2-hydroxy-3-isopropylaminopropoxy)isoquinoline hydrogen maleate having an M.P. of 166°-167°.

EXAMPLE 3

1-(2-hydroxy-3-isopropylaminopropoxy)-6-methoxy-isoquinoline [process variant b)]

25 cc of 1 N hydrochloric acid are added to 3.0 g of 1-(3-isopropyl-2-phenyl-5-oxazolidinylmethoxy)-6-methoxy-isoquinoline, and the mixture is stirred at room temperature for 2 hours. Working up is effected in a manner analogous to that described in Example 1. 1-(2-hydroxy-3-isopropylaminopropoxy)-6-methoxy-isoquinoline, having an M.P. of 95°-97°, is obtained.

The following compounds of formula I are obtained in a manner analogous to that described in Examples 1 to 3 by a ring opening in the corresponding 1-(5-oxazolidinylmethoxy)isoquinolines:

| Example | R | $R_1$ | $R_2$ | | M.P. |
|---|---|---|---|---|---|
| 4 | CH(CH₃)₂ | 5-CH₃O | H | (hydrogen maleate) | 158–160° |
| 5 | CH(CH₃)₂ | 3-CH₃ | H | (hydrogen maleate) | 150–151° |
| 6 | CH(CH₃)₂ | 7-CH₃ | H | (hydrogen maleate) | 164–168° |
| 7 | CH(CH₃)₂ | 4-CH₃ | H | (hydrogen maleate) | 139–140° |
| 8 | cyclobutyl | H | H | (hydrogen maleate) | 178–180° |
| 9 | C(CH₃)₃ | H | H | (hydrogen maleate) | 180° |
| 10 | adamantyl | H | H | (hydrogen maleate) | 166–167° |
| 11 | CH₂—CH(CH₃)₂ | H | H | (hydrogen maleate) | 178–180° |
| 12 | CH₂—C(CH₃)₃ | H | H | (hydrogen maleate) | 115–117° |
| 13 | CH₂CH₂—phenyl | H | H | (hydrochloride) | 121–123° |
| 14 | CH(CH₃)₂ | 6-CH₃O | 7-CH₃O | (base) | 98–100° |
| 15 | C(CH₃)₃ | 4-CH₃O | H | (base) | 134–136° |
| 16 | CH(CH₃)₂ | 7-Cl | H | (hydrogen maleate) | 160–163° |
| 17 | CH(CH₃)₂ | 7-CH(CH₃)₂ | H | (hydrogen maleate) | 141–143° |
| 18 | CH(CH₃)₂ | 7-CF₃ | H | (hydrogen maleate) | 171–173° |
| 19 | cyclopropyl | H | H | (bis[base]fumarate) | |
| 20 | C(CH₃)₂—C≡CH | H | H | (bis[base]fumarate) | 176–177° |
| 21 | CH(CH₃)₂ | 5-NO₂ | H | (hydrogen maleate) | 155–157° |
| 22 | CH(CH₃)₂ | 5-NHCOCH₃ | H | (base) | 153–55° |
| 23 | CH₂CH₂—(2,6-dimethoxyphenyl, OCH₃/OCH₃) | H | H | (bis[base]fumarate) | 168–69° |
| 24 | C(CH₃)₂C₂H₅ | H | H | (hydrogen maleate) | 151–53° |
| 25 | C(CH₃)₂CH=CH₂ | H | H | | |
| 26 | C(CH₃)₂CH₂OH | H | H | (bis[base]naphthalene-1,5-disulphonate) | 168–171° |
| 27 | C(CH₃)₃ | 7-Cl | H | (hydrogen maleate) | 200–202° |
| 28 | C(CH₃)₃ | 7-CH₃O | H | (hydrogen maleate) | 190–192° |
| 29 | C(CH₃)₃ | 7-F | H | | |
| 30 | CH(CH₃)₂ | 7-Br | H | | |
| 31 | 1-methylcyclohexyl (—CH₃) | H | H | | |
| 32 | —CH₂—CH₂—C₆H₄—Cl | H | H | | |
| 33 | —CH₂—CH₂—C₆H₄—CH₃ | H | H | | |
| 34 | C(CH₃)₃ | 5-NHCHO | H | | |
| 35 | C(CH₃)₃ | 5-CH₃ | 7-CH₃ | | |
| 36 | C(CH₃)₃ | 3-CH₃ | 6-CH₃ | | |
| 37 | —C(C₂H₅)₂C≡CH | H | H | Bis(base)fumarate | 148–9° |

EXAMPLE 38

1-[2-hydroxy-3-(2-methyl-3-butin-2-ylamino)propoxy]-isoquinoline [process variant a)]

0.86 g of potassium are dissolved in 40 cc of tert.butyl alcohol, and 3.8 g of 1-(2-methyl-3-butinylamino)-2,3-dihydroxypropanol and then 3.6 g of 1-chloroisoquinoline are added. After stirring for 1 day, heating is effected to 50° for a further day. The reaction solution is concentrated in a vacuum. The residue is taken up in 1 N hydrochloric acid and ether, the aqueous phase is neutralized with a 2 N soda solution and extracted with methylene chloride. After drying over magnesium sulphate and concentrating, an oil is obtained which gives the bis-fumarate of the title compound, having an M.P. of 176°–177°, with fumaric acid in methylene chloride and ether.

The required 1-(2-methyl-3-butinylamino)-2,3-dihydroxypropanol is obtained by reaction of glycidol with an equimolar amount of 2-amino-2-methyl-3-butine in ethanol.

The compounds of formula I described in Examples 1 to 24 and 26 to 37 are obtained in a manner analogous to that described in Example 38 by reacting the corresponding compound of formula II with the corresponding compound of formula III, using process variant (a).

The following compounds of formula I are obtained in a manner analogous to that described in Examples 1 and 38 but employing appropriate starting materials in appropriate amounts.

| Example | R | $R_1$ | $R_2$ | M.P. |
|---|---|---|---|---|
| 39 | —C(CH₃)₃ | 4-CH₃ | H | (fumarate) 215 – 216 |
| 40 | —C(CH₃)₂—benzyl | H | H | (naphthalene-1,5-disulphonate) 230 – 232 |
| 41 | —C(CH₃)₃ | 7-Br | H | (hydrogen maleate) 183 – 186 |
| 42 | —C(CH₃)₃ | 7-C(CH₃)₃ | H | (naphthalene-1,5-disulphonate) 210 – 213 |
| 43 | —C(CH₃)₃ | 4-NO₂ | H | (hydrogen maleate) 193 – 195 |

-continued

| Example | R | R₁ | R₂ | M.P. |
|---|---|---|---|---|
| 44 | —C(CH₃)₃ | 6-CH₃ | H | (fumarate) 118 – 120 |
| 45 | —C(CH₃)₃ | 5-CH₃ | H | (fumarate) 116 – 118 |
| 46 | —C(CH₃)₃ | 7-CH₃ | 4-CH₃ | (fumarate) 202 – 204 |

The compounds of formula I are useful because they posses pharmacological activity in animals. In particular, the compounds are useful as adrenergic β-blocking agents, e.g. in the prophylaxis and therapy of coronary diseases, particularly in the treatment of Angina pectoris, the hyperkinetic heart syndrome and conditions resulting from muscular hypertrophic subvalvular aortostenosis, and also as antiarrhythmic agents, e.g. in the treatment of heat rhythm disorders, as indicated in standard tests, e.g. by an inhibition of the positive inotropic adrenalin effect in the spontaneously beating guinea pig atrium at a bath concentration of from 0.005 to 2.5 mg/liter, and a prolonged inhibition of the tachycardia and hypotension caused by isoproterenol [1-(3,4-dihydroxyphenyl)-2-isopropylaminoethanol] in the infusion test in the anaesthetized dog at an effective cumulative dose, administered intravenously by infusion, of from 0.02 to 0.6 mg/kg animal body weight.

For the above-mentioned uses, the dosage administered will, of course, vary depending on the compound employed, mode of administration and treatment desired. However, in general, satisfactory results are obtained when administered, e.g. orally or parenterally, at a daily dosage of from about 0.01 to 1.5 mg/kg animal body weight, which may, if necessary, be administered in divided form twice daily. For the larger mammals, the total daily dosage is in the range of from about 1 to 100 mg, and dosage forms suitable for oral administration comprise from about 5 to 50 mg of the compound, admixed with a solid or liquid pharmaceutical carrier or diluent.

The compounds of formula I are furthermore useful as inhibitors of hyperlipoidemia induced by emotional stress and also as agents for the treatment or prophylaxis of myocardism as indicated in standard tests for showing inhibition of increased free fatty acid concentration due to mobilisation, and lipolysis, in blood induced by emotional stress, for example, by an inhibition of glycerol release stimulated by isoproterenol (i) in vitro, e.g. at a concentration of about 0.1 to about 10 mg/l solution of the compounds in fat cells of the epididymal fat tissue of rats, the cells having been isolated in accordance with the method of M. Rodbell [J. biol.chem. 239, 375-80 (1946)], and ii) in vivo, e.g. in rats on s.c. administration of from about 0.1 to about 1 mg/kg animal body weight of the compounds.

The compounds of formula I are furthermore useful as inhibitors of hyperglycemia induced by emotional stress and therefore as suppressants of appetite induced by emotional stress, as indicated in standard tests, e.g. by an inhibition of glucose release stimulated by isoproterenol in rats in vivo on s.c. administration of from about 0.1 to about 10 mg/kg animal body weight of the compounds.

For the above-mentioned uses for stress conditions the dosage will, of course, vary depending on the compound employed, mode of administration and treatment desired. However, in general, satisfactory results are obtained when administered at a daily dosage of from about 0.01 mg to about 5 mg/kg animal body weight, conveniently given in divided doses 2 to 4 times a day or in sustained release form. For the larger mammals, the total daily dosage is in the range from about 1 to about 200 mg, and dosage forms suitable for oral administration comprise from about 0.25 mg to about 100 mg of the compounds admixed with a solid or liquid pharmaceutical carrier or diluent.

Especially suitable for the latter use are compounds of formula I wherein R is a radical branched in an α-position to the nitrogen atom to which R is bound; especially interesting are compounds of formula I wherein R is bound to the nitrogen atom with a tertiary carbon atom.

The compounds of Examples 2, 9, 16, 20 and 27 are especially interesting compounds.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

A group of compounds have the formula

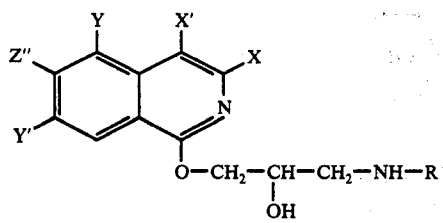

wherein
(i) each of X, X', Y, Y' and Z" are hydrogen, or
(ii) one of X, X', Y and Y' is methyl and the others of X, X', Y and Y' together with Z" are hydrogen, or
(iii) one of Y, Y' and Z" is methoxy and the others of Y, Y' and Z" together with X and X' are hydrogen, and
R is alkyl, cycloalkyl or phenethyl.

In another group $R_2$ is in the 6 or 7 position.

What is claimed is:

1. A compound of formula I,

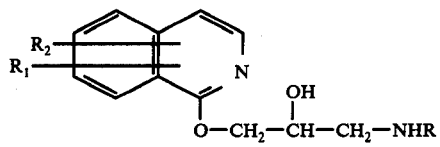

wherein
R is lower alkyl or cycloalkyl of 3 to 7 carbon atoms; cycloalkyl of 3 to 7 carbon atoms substituted by alkyl of 1 to 4 carbon atoms; α-dialkylpropinyl or α-dialkylallyl of 5 to 9 carbon atoms, hydroxyalkyl of 2 to 7 carbon atoms, the hydroxy group thereof being separated by at least two carbon atoms from the nitrogen atom to which R is bound; phenethyl; phenethyl substituted by halogen, alkyl or alkoxy of 1 to 4 carbon atoms; ot adamantyl, $R_1$ is hydrogen, halogen, alkyl or alkoxy of 1 to 4 carbon atoms, trifluoromethyl in the 5, 6 or 7 position, or a nitro or A—NH— group in the 4 or 5 position, wherein A is formyl or alkanoyl of 2 to 4 carbon atoms, and $R_2$ is hydrogen, or, when $R_1$ is alkyl of 1 to 4 carbon atoms, also alkyl of 1 to 4 carbon atoms, or, when $R_1$ is alkoxy of 1 to 4 carbon atoms, also alkoxy of 1 to 4 carbon atoms, with the general proviso that the 8 position of the isoquinoline ring is unsubstituted, and any halogen substituent which may present in the 3 or 4 position is other than fluorine, or a pharmaceutically acceptable acid addition salt thereof.

2. A method of treating hyperglycemia induced by stress in animals, which comprises administering to an animal in need of such treatment a therapeutically effective amount of a compound of claim 1.

3. A compound of claim 1 having the formula,

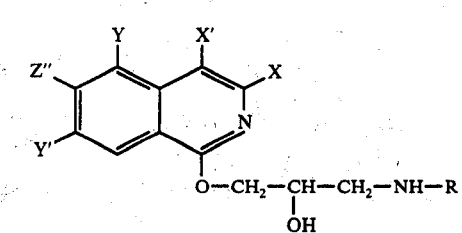

wherein
(i) each of X, X', Y, Y' and Z" are hydrogen, or
(ii) one of X, X', Y and Y' is methyl and the others of X, X', Y and Y' together with Z" are hydrogen, or
(iii) one of Y, Y' and Z" is methoxy and the others of Y, Y' and Z" together with X and X' are hydrogen, and R is alkyl, cycloalkyl or phenethyl.

4. A compound of claim 3, wherein R is isopropyl.

5. A compound of claim 1, wherein R is a radical branched in the α position to the nitrogen atom to which R is bound.

6. A compound of claim 5, wherein R is bound to the nitrogen atom with a tertiary carbon atom.

7. The compound of claim 1, which is 1-(2-hydroxy-3-isopropylaminopropoxy)-7-methoxyisoquinoline.

8. The compound of claim 1, which is 1-(2-hydroxy-3-isopropylaminopropoxy)-isoquinoline.

9. The compound of claim 1, which is 1-(2-hydroxy-3-isopropylaminopropoxy)-6-methoxyisoquinoline.

10. The compound of claim 1, wherein R, $R_1$ and $R_2$ are respectively $CH(CH_3)_2$, 5—$CH_3O$, H.

11. The compound of claim 1, wherein R, $R_1$ and $R_2$ are respectively $CH(CH_3)_2$, 3—$CH_3$, H.

12. The compound of claim 1, wherein R, $R_1$ and $R_2$ are respectively $CH(CH_3)_2$, 7—$CH_3$, H.

13. The compound of claim 1, wherein R, $R_1$ and $R_2$ are respectively $CH(CH_3)_2$, 4—$CH_3$, H.

14. The compound of claim 1, wherein R, $R_1$ and $R_2$ are respectively

,

H, H.

15. The compound of claim 1, wherein R, $R_1$ and $R_2$ are respectively $C(CH_3)_3$, H, H.

16. The compound of claim 1, wherein R, $R_1$ and $R_2$ are respectively adamantyl, H, H.

17. The compound of claim 1, wherein R, $R_1$ and $R_2$ are respectively $CH_2$—$CH(CH_3)_2$, H, H.

18. The compound of claim 1, wherein R, $R_1$ and $R_2$ are respectively $CH_2$—$C(CH_3)_3$, H, H.

19. The compound of claim 1, wherein R, $R_1$ and $R_2$ are respectively

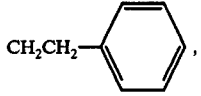,

H, H.

20. The compound of claim 1, wherein R, $R_1$ and $R_2$ are respectively $CH(CH_3)_2$, 6—$CH_3O$, 7—$CH_3O$.

21. The compound of claim 1, wherein R, $R_1$ and $R_2$ are respectively $C(CH_3)_3$, 4—$CH_3O$, H.

22. The compound of claim 1, wherein R, $R_1$ and $R_2$ are respectively $CH(CH_3)_2$, 7—Cl, H.

23. The compound of claim 1, wherein R, $R_1$ and $R_2$ are respectively $CH(CH_3)_2$, 7—$CH(CH_3)_2$, H.

24. The compound of claim 1, wherein R, $R_1$ and $R_2$ are respectively $CH(CH_3)_2$, 7—$CF_3$, H.

25. The compound of claim 1, wherein R, $R_1$ and $R_2$ are respectively

H, H.

26. The compound of claim 1, wherein R, $R_1$ and $R_2$ are respectively $C(CH_3)_2$-C≡CH, H, H.

27. The compound of claim 1, wherein R, $R_1$ and $R_2$ are respectively $CH(CH_3)_2$, 5—$NO_2$, H.

28. The compound of claim 1, wherein R, $R_1$ and $R_2$ are respectively $CH(CH_3)_2$, 5—$NHCOCH_3$, H.

29. The compound of claim 1, wherein R, $R_1$ and $R_2$ are respectively

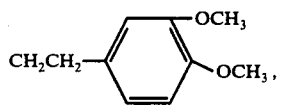

H, H.

30. The compound of claim 1, wherein R, $R_1$ and $R_2$ are respectively $C(CH_3)_2C_2H_5$, H, H.

31. The compound of claim 1, wherein R, $R_1$ and $R_2$ are respectively $C(CH_3)_2CH=CH_2$, H, H.

32. The compound of claim 1, wherein R, $R_1$ and $R_2$ are respectively $C(CH_3)_2CH_2OH$, H, H.

33. The compound of claim 1, wherein R, $R_1$ and $R_2$ are respectively $C(CH_3)_3$, 7—Cl, H.

34. The compound of claim 1, wherein R, $R_1$ and $R_2$ are respectively $C(CH_3)_3$, 7—$CH_3O$, H.

35. The compound of claim 1, wherein R, $R_1$ and $R_2$ are respectively $C(CH_3)_3$, 7—F, H.

36. The compound of claim 1, wherein R, $R_1$ and $R_2$ are respectively $CH(CH_3)_2$, 7—Br, H.

37. The compound of claim 1, wherein R, $R_1$ and $R_2$ are respectively

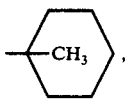

H, H.

38. The compound of claim 1, wherein R, $R_1$ and $R_2$ are respectively

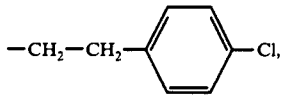

H, H.

39. The compound of claim 1, wherein R, $R_1$ and $R_2$ are respectively

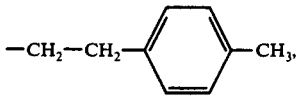

H, H.

40. The compound of claim 1, wherein R, $R_1$ and $R_2$ are respectively $C(CH_3)_3$, 5—NHCHO, H.

41. The compound of claim 1, wherein R, $R_1$ and $R_2$ are respectively $C(CH_3)_3$, 5—$CH_3$, 7—$CH_3$.

42. The compound of claim 1, wherein R, $R_1$ and $R_2$ are respectively $C(CH_3)_3$, 3—$CH_3$, 6—$CH_3$.

43. The compound of claim 1, wherein R, $R_1$ and $R_2$ are respectively —$C(C_2H_5)_2$C≡CH, H, H.

44. The compound of claim 1, wherein R, $R_1$ and $R_2$ are respectively $C(CH_3)_3$, 4—$CH_3$, H.

45. The compound of claim 1, wherein R, $R_1$ and $R_2$ are respectively $C(CH_3)_2$-benzyl, H, H.

46. The compound of claim 1, wherein R, $R_1$ and $R_2$ are respectively $C(CH_3)_3$, 7—Br, H.

47. The compound of claim 1, wherein R, $R_1$ and $R_2$ are respectively $C(CH_3)_3$, 7—$C(CH_3)_3$, H.

48. The compound of claim 1, wherein R, $R_1$ and $R_2$ are respectively $C(CH_3)_3$, 4—$NO_2$, H.

49. The compound of claim 1, wherein R, $R_1$ and $R_2$ are respectively $C(CH_3)_3$, 6—$CH_3$, H.

50. The compound of claim 1, wherein R, $R_1$ and $R_2$ are respectively $C(CH_3)_3$, 5—$CH_3$, H.

51. The compound of claim 1, wherein R, $R_1$ and $R_2$ are respectively $C(CH_3)_3$, 7—$CH_3$, 4—$CH_3$.

52. A pharmaceutical composition useful for treating hyperglycemia, hyperlipidemia or Angina pectoris comprising a compound of claim 1 in association with a pharmaceutical carrier or diluent.

* * * * *